United States Patent
Heide et al.

(10) Patent No.: US 12,285,726 B2
(45) Date of Patent: Apr. 29, 2025

(54) USE OF A FILTER MODULE FOR FILTERING A BIOTECHNICAL LIQUID AND FILTER MODULE FOR THE FILTRATION OF A BIOTECHNICAL LIQUID

(71) Applicants: FRESENIUS MEDICAL CARE DEUTSCHLAND GMBH, Bad Homburg (DE); UNICYTE EV AG, Oberdorf (CH)

(72) Inventors: Alexander Heide, Eppstein (DE); Dejan Nikolic, Bad Soden (DE)

(73) Assignees: FRESENIUS MEDICAL CARE DEUTSCHLAND GMBH, Bad Homburg (DE); UNICYTE EV AG, Oberdorf Nidwalden (CH)

( * ) Notice: Subject to any disclaimer, the term of this patent is extended or adjusted under 35 U.S.C. 154(b) by 0 days.

(21) Appl. No.: 17/768,866

(22) PCT Filed: Nov. 5, 2020

(86) PCT No.: PCT/EP2020/081082
§ 371 (c)(1),
(2) Date: Apr. 14, 2022

(87) PCT Pub. No.: WO2021/094185
PCT Pub. Date: May 20, 2021

(65) Prior Publication Data
US 2023/0142123 A1    May 11, 2023

(30) Foreign Application Priority Data
Nov. 12, 2019   (EP) ..................................... 19208713

(51) Int. Cl.
*A61M 60/232*   (2021.01)
*A61M 60/824*   (2021.01)
(Continued)

(52) U.S. Cl.
CPC ....... *B01D 63/0222* (2022.08); *A61M 60/232* (2021.01); *F04D 13/024* (2013.01); *A61M 60/824* (2021.01)

(58) Field of Classification Search
CPC ........ F04D 13/024; F04D 1/00; F04D 29/406; A61M 1/267; A61M 60/232; B01D 63/0222
See application file for complete search history.

(56) References Cited

U.S. PATENT DOCUMENTS

| 5,263,924 | A | 11/1993 | Mathewson |
| 5,830,370 | A | 11/1998 | Maloney, Jr. et al. |

(Continued)

FOREIGN PATENT DOCUMENTS

| CA | 2613610 A1 * | 6/2008 | .......... A61M 1/1006 |
| DE | 3923692 A1 * | 1/1991 | .............. A61M 1/14 |

(Continued)

OTHER PUBLICATIONS

Reul et al., "Medical Blood Treatment Apparatus . . . "—(DE_3923692_A1_I_MT.pdf), Jan. 1991 (Year: 1991).*

(Continued)

*Primary Examiner* — Kenneth J Hansen
(74) *Attorney, Agent, or Firm* — Kilyk & Bowersox, P.L.L.C.

(57) ABSTRACT

A filter module provides biotechnological filtration possibilities lessening the danger of contamination while achieving an optimum flow profile. The filter module 100 includes filter housing 110, a filter with a bundle of hollow fibres 114 and a centrifugal pump rotor 132. The filter is arranged in the filter housing 110 such that the centrifugal pump rotor 132 forces a biotechnological liquid into the interior of the hollow fibres 114 via an inlet flow path where liquid enters the filter module perpendicular to a longitudinal axis of the (Continued)

filter, flows into a hollow centre of the centrifugal pump rotor and is thereafter deflected to flow parallel to the longitudinal axis of the filter before entering the hollow fibers of the filter flowing parallel to the longitudinal axis. A filtration device 1100, 1200, 1300 includes filter module 100 and a drive unit for magnetically driving the centrifugal pump rotor 132.

19 Claims, 6 Drawing Sheets

(51) Int. Cl.
*B01D 63/02* (2006.01)
*F04D 13/02* (2006.01)

(56) References Cited

U.S. PATENT DOCUMENTS

| | | |
|---|---|---|
| 6,623,441 B1 | 9/2003 | Kihara et al. |
| 7,871,566 B2 | 1/2011 | Strauss et al. |
| 8,647,569 B1 | 2/2014 | Federspiel et al. |
| 9,345,826 B2 * | 5/2016 | Kenley .................. A61M 1/16 |
| 10,426,884 B2 * | 10/2019 | Labib .................. A61M 1/3647 |
| 2002/0020931 A1 * | 2/2002 | Stowell ................ A61K 9/1273 |
| | | 264/4.1 |
| 2002/0039596 A1 | 4/2002 | Hartounian et al. |
| 2004/0223872 A1 * | 11/2004 | Brian .................. B01D 19/0031 |
| | | 604/6.14 |
| 2011/0002794 A1 * | 1/2011 | Haefliger ............ F04D 29/0413 |
| | | 415/203 |
| 2019/0125946 A1 * | 5/2019 | Gartner ................ A61M 60/232 |
| 2019/0211831 A1 * | 7/2019 | Sinico .................. F04D 13/0606 |

FOREIGN PATENT DOCUMENTS

| | | |
|---|---|---|
| DE | 60207411 T2 | 6/2006 |
| EP | 0576677 A1 | 1/1994 |
| EP | 1398047 A1 | 3/2004 |
| JP | 2001300263 A | 10/2001 |
| JP | 2010285438 A | 12/2010 |
| WO | 2017117585 A1 | 7/2017 |

OTHER PUBLICATIONS

International Search Report and Written Opinion issued in corresponding International Patent Application No. PCT/EP2020/081082 (with English translation of International Search Report) mailed Jan. 18, 2021 (14 pages).

Office Action issued in corresponding Japanese Patent Application No. 2022-527168 dated Jul. 22, 2024 (with English translation) (10 pages).

Office Action issued in corresponding Taiwan Patent Application No. 109136131 dated Jun. 19, 2024 (with English translation (20 pages).

* cited by examiner

USE OF A FILTER MODULE FOR FILTERING A BIOTECHNICAL LIQUID AND FILTER MODULE FOR THE FILTRATION OF A BIOTECHNICAL LIQUID

This application is a National Stage Application of PCT/EP2020/081082, filed Nov. 5, 2020, which claims priority to European Patent Application No. 19208713.8, filed Nov. 12, 2019.

The present invention relates to the use of a filter module and to a filter module for the filtration of a biotechnological liquid and to a filtration device having such a filter module.

Biotechnological methods for the processing of biotechnological liquids are known from the prior art, for example for purifying or treating biotechnological liquids by a TFF (tangential flow filtration) method. In the latter, similarly to dialysis, a substrate liquid is circulated and, by means of a pump, is conveyed several times through a hollow-fibre membrane module. Some of the liquid and also small molecules pass through the membrane to the permeate side. Permeate is the name given to the substance passing through the membranes. The permeate side is the outer side of a hollow fibre when the primary biotechnological liquid is conveyed into the interior of the hollow fibre. The volume of the part of the liquid that remains in the circuit and does not pass through the membranes of the hollow fibres thus decreases. This part of the liquid is called the retentate. The decrease in the volume of the retentate therefore means that the biotechnological materials to be purified in the reduced volume, cleared of the small molecules, remain in the retentate on the retentate side. In other words, the concentration of the desired constituents in the retentate is increased as permeate is precipitated.

A TFF method of this kind, which in a preferred embodiment is the subject matter of the present invention, is known from WO 2017/117585 A1, for example.

Moreover, centrifugal pumps and pump devices with centrifugal pumps are known which have rotatable components within the interior of a pump head, wherein a medium that is to be conveyed is entrained by the rotation of said components and is thus also set in rotation. As a result of the rotational movement, centripetal forces, manifested in a rotating reference system as centrifugal forces, act on the entrained medium that is to be conveyed. When the medium to be conveyed passes near the rotation axis into the interior of such a centrifugal pump, it is forced outwards by the centrifugal forces on account of the rotation and thereby conveyed, in other words pumped.

The problem in known biotechnological filtration methods and filtration devices is that, when setting up a flow diagram or flow circuit for the filtration, a pump and a filter are interconnected, resulting in the formation of a dead space or edges in which eddies occur, having a negative impact on the flow profile and constituting danger points for contamination. A mechanical interface is usually required for connecting a pump to a filter. A flange is normally used for this purpose. Devices are also known in which a line section additionally lies between centrifugal pump rotor and filter. In such connections, there are at least two interfaces, e.g. flanges, between the centrifugal pump rotor and the filter, with the abovementioned disadvantages. In other words, this means that there are two points of entry for contamination, accordingly with reduced hygiene and even more dead space for liquid.

It is therefore an object of the present invention to provide biotechnological filtration possibilities with which the risk of contamination is low and at the same time an optimum flow profile can be achieved.

This object is achieved by the use of a filter module which has in a filter housing a filter, with a bundle of hollow fibres, and a centrifugal pump rotor, for a biotechnological production method according to Claim 1. This object is also achieved by a filter module for the filtration of a biotechnological liquid according to Claim 6 and by a filtration device according to Claim 14.

The use of a filter module which has in a filter housing a filter, with a bundle of hollow fibres, and a centrifugal pump rotor for a biotechnological production method is disclosed.

Also disclosed is a filter module for the filtration of a biotechnological liquid, which has a housing, a filter arranged in the housing with a bundle of hollow fibres, a centrifugal pump rotor arranged in the housing such that it is fluidically connected to the interior of the hollow fibres, wherein the centrifugal pump rotor is able to be magnetically driven such that it can force a liquid through the hollow fibres, a first port for the supply of a biotechnological liquid to be filtered, which first port is fluidically connected to the interior of the hollow fibres of the filter, a second port for the removal of a biotechnological liquid to be filtered, which second port is fluidically connected to the interior of the hollow fibres of the filter, and a third port for the removal of precipitated waste liquid, which third port is fluidically connected to the exterior of the hollow fibres.

According to one aspect of the invention, such a filter module can be used in particular for a biotechnological filtration method, in particular a tangential flow filtration (TFF) method, a method for the filtration or concentration of extracellular vesicles in a biotechnological liquid, or a tangential flow filtration (TFF) method for the filtration or concentration of biological macromolecules and biological microstructures, in particular extracellular vesicles, in a biotechnological liquid.

This use of a filter module which has in a filter housing a filter, with a bundle of hollow fibres, and a centrifugal pump rotor, for a biotechnological production method, and the filter module for the filtration of a biotechnological liquid which has a housing, with a centrifugal pump rotor arranged therein, and a filter arranged in the housing with a bundle of hollow fibres, particularly advantageously permits increased hygiene and reduced contamination, since there is no mechanical interface for connection between centrifugal pump rotor and filter.

In the use according to the invention, the fibres of the fibre bundle of the filter are preferably oriented vertically with respect to the earth's surface, i.e. parallel to the direction of the local force of gravity, and the centrifugal pump rotor is arranged on the longitudinal axis of the bundle coaxially below the bundle such that, during the operation of the pump, the liquid flows upwards. A vertical arrangement of the centrifugal pump rotor and the filter fibres affords the advantage that any gas accumulations present in the liquid are transported away upwards by buoyancy and at the same time by the liquid flow generated by the pump. Such gas accumulations are undesired. The fibres of the filter are preferably arranged parallel to the rotation axis of the centrifugal pump rotor. The centrifugal pump rotor is in this case arranged downstream from the filter. The filter is preferably situated above the centrifugal pump rotor in relation to a plane on which the device stands. In other words, liquid is pumped from the centrifugal pump rotor to the filter counter to the direction of gravity. This has in particular the advantage that, assisted by the direction of flow of the fluid, gas bubbles rise upwards counter to the force of gravity.

The centrifugal pump rotor is preferably an impeller rotor that can be supported by magnetic levitation and can be driven magnetically. In such a design, the supporting and driving of the centrifugal pump rotor are purely magnetic. There are therefore no mechanical bearings. There is therefore also no local heat source, as there would be in the case of a mechanical bearing of a centrifugal pump rotor with a shaft or an axle, on account of frictional forces. This affords the advantage of reduced damage to the biotechnological liquid that comes into contact with the centrifugal pump rotor. Heat, after all, is damaging to the vast majority of biotechnological liquids.

In a filter according to the invention, the bundle of fibres is arranged such that the fibres extend parallel to one another. The fibres can have an undulation or can be straight. Even when they have an undulation, they extend approximately straight when seen macroscopically. A longitudinal axis of a filter extends parallel to the fibres of the bundle. If the bundle corresponds to a cylindrical arrangement of fibres, the longitudinal axis is to be equated with the rotation axis of the cylinder. A filter housing of a filtration device according to the invention is accordingly elongate, and its longitudinal direction extends along the longitudinal axis of such a bundle.

Each hollow fibre of a fibre bundle defines a cavity in its interior. Between the cavity in the interior of a fibre and the exterior of a fibre lies the wall of the fibre. The wall is preferably a membrane. The membrane is preferably porous. If a filter is formed from a bundle of hollow fibres, the membranes of the fibres form the membrane of the filter.

According to one aspect of the present application, with regard to the use of a filter module which has in a filter housing a filter, with a bundle of hollow fibres, and a centrifugal pump rotor, for a biotechnological production method, and with regard to a filter module for the filtration of a biotechnological liquid or a filtration device, a filter of the filter module preferably has an exclusion limit, or molecular weight cut-off (MWCO), of 100-1000 kDa. An exclusion limit in this range for example particularly advantageously permits biotechnological production methods or biotechnological filtration methods. In other words, in this preferred case, the membrane of the filter has an exclusion limit in the range of 100-1000 kDa.

In the context of this application, the use of a filter module, a filter module and a filtration device are to be understood with respect to biological liquids and biotechnological liquids. Biotechnical is to be regarded as a shortened form of biotechnological and is therefore equivalent in meaning. Since no differentiation between biological liquid and biotechnological liquid is generally established, both are regarded as liquids with biological constituents. Biotechnical is a shortened form of biotechnological and is equivalent in meaning.

For the use of a filter module having a filter housing, a filter, with a bundle of hollow fibres, and a centrifugal pump rotor, for a biotechnological production method, and for a filter module for the filtration of a biotechnological liquid having a housing, a filter, with a bundle of hollow fibres, and a centrifugal pump rotor arranged in the housing, it is essential in the context of the present application that there are at least three ports on the filter housing, through which ports the biotechnological liquid or the precipitated waste liquid is conducted. At least two ports are fluidically connected to the interior of the hollow fibres of the fibre bundle of the filter, and at least one port is fluidically separated from the interior of the hollow fibres of the fibre bundle of the filter but at the same time fluidically connected to the exterior of the hollow fibres of the fibre bundle. The at least two ports connected to the interior are arranged such that they are arranged at the opposite ends of the fibres. In other words, if a liquid flows through the fibre bundle in one direction, one port connected to the interior lies upstream from the fibre bundle, and the other port connected to the interior lies downstream from the fibre bundle. This is necessary because the two ports connected to the interior of the hollow fibres serve to permit the flow of a liquid along the fibres through the interior. The third port is fluidically connected to the exterior of the fibres but not to the interior. It serves to remove liquid from the exterior of the fibres. In the use for a biotechnological production method, the liquid that has passed through the fibres is usually regarded as waste. The aim is to remove this liquid from the biotechnological liquid and thereby concentrate the latter. The liquid that has passed through the fibres is also referred to as permeate. The permeate can be removed through a third port, which is arranged on the filter housing. This third port can be arranged on a first end cap, on a second end cap or on a middle part. It is essential for this third port that it is fluidically connected to the exterior of the fibres of the fibre bundle of the filter and that at the same time it is not fluidically connected directly and completely to the interior of the hollow fibres of the fibre bundle, but instead is separated from the interior of the hollow fibres of the fibre bundle by the wall of the hollow fibres, i.e. the membrane.

The centrifugal pump rotor is preferably an impeller. That is to say, the centrifugal pump is equipped with a radially pumping pump wheel, and this pump wheel is configured as an impeller. The pump wheel is also called the running wheel of the pump. An impeller can preferably be configured with a hollow centre. For example, such an impeller can be substantially disc-shaped and have substantially radially extending blades which, during a rotation movement of the pump wheel, entrain a pumped medium that is to be conveyed. That is to say, a first disc forms a base on which blades are arranged. In other words, the blades stand on the first disc. The end of the blades remote from the first disc plane can in turn be connected to a further disc, arranged parallel to the first disc. Optionally, therefore, a second disc can connect those ends of the blades opposite from the first disc, that is to say they can form a closure. The second disc is then parallel to the first disc, and the blades lie between the two discs. An embodiment with two discs arranged parallel to each other is just as conceivable as an embodiment with only one disc on which the blades are arranged, while the end of the blades remote from the disc is free. A first variant of such a disc has a central clearance, i.e. it is roughly speaking ring-shaped. An alternative variant of such a disc is configured as a circular disc, i.e. it has no central clearance.

In the context of the present application, an impeller with a hollow centre is to be understood as meaning that the blades do not extend to the centre as far as the rotation axis, but instead a macroscopically perceptible region at and/or directly around the rotation axis of the impeller is free of blades. However, the hollow centre is also not filled with a solid three-dimensional body, for example a solid cylinder. Instead, the centre is hollow, such that the liquid to be pumped can flow through the hollow centre. It is conceivable that a solid body lies exactly on the rotation axis of the pump wheel, e.g. an axle or a shaft. The hollow centre is then the region lying centrally around the rotation axis between the solid body and the blades, i.e. the region through which the liquid to be pumped can flow freely. The hollow centre can then be configured, for example, substantially as a cylinder jacket with finite jacket thickness.

In a preferred embodiment, the housing of the filter module has an inner supporting plate with openings, which are arranged between the centrifugal pump rotor and the filter bundle such that liquid flows from the centrifugal pump rotor through the openings and then to the fibres of the filter when the centrifugal pump rotor has been set in rotation.

According to one aspect of the present application, the centrifugal pump rotor and the fibre bundle of a filter module are arranged coaxially. This permits a particularly symmetrical flow of a liquid through the centrifugal pump rotor into the interior of the hollow fibres of the fibre bundle. Antiparallel, coaxial flows of liquid then exist in some sections in such a situation. The liquid flows onto the centrifugal pump rotor on the longitudinal axis of the fibre bundle, which is coincident with the rotation axis of the centrifugal pump rotor, and, after leaving the centrifugal pump rotor, is deflected such that it flows in parallel but with opposite directionality to the fibre bundle. The fibre bundle is preferably approximately cylindrical at the macroscopic level. The centrifugal pump rotor is hydraulically stabilized by this symmetrical flow arrangement. This minimizes a potential fluttering of the centrifugal pump rotor. Fluttering of the centrifugal pump rotor could lead to the biotechnological liquid being damaged. Thus, possible damage to the biotechnological liquid is also avoided. Particularly in the case of centrifugal pump rotors supported by magnetic levitation, according to a further aspect of the present application there is also the advantage that less eccentric bearing moments occur, or the eccentric bearing moments are less strong. Therefore, less strong magnetic fields suffice for driving and supporting the centrifugal pump rotor. The less strong magnetic fields in turn mean that less energy and/or less electric current is needed in the generator of the magnetic alternating fields of the drive unit.

In the context of the present application, as regards a filter module or a filtration device having a filter module, wherein a centrifugal pump rotor supported by magnetic levitation is arranged in the filter housing, provision can be made that a fully functional centrifugal pump is formed only when the filter module is coupled to the filtration device such that the drive unit of the filtration system can drive the centrifugal pump rotor by means of dynamic magnetic fields and/or can support the same by magnetic levitation. In other words, if the drive unit and the filter module are not coupled, no functional pump is formed. The centrifugal pump rotor is not in itself a complete, functional pump. Similarly, the drive unit of a filtration device without a centrifugal pump rotor is not a complete functional pump.

The biotechnological production method can be a filtration. In a filtration by a biotechnological method, a biotechnological liquid, for example, is filtered, purified or conditioned.

In the context of the present application, a biotechnological liquid is also to be understood as a biological liquid. Thus, for example, a biological liquid can become the biotechnological liquid by a biotechnological method. Therefore, in the context of this application, when the use of a filter module for a biotechnological method is mentioned, this is to be understood as covering methods in which a starting liquid of a method is a biotechnological liquid or a biological liquid. Analogously, in the context of this application, the expression "filter module for the filtration of a biotechnological liquid" is to be understood as also meaning a "filter module for the filtration of a biological liquid". If a liquid is filtered, some of the liquid constituents pass through a filter. Consequently, the constituents of the liquid that do not pass through the filter are concentrated. Depending on which constituents of a liquid are desirable, such a method also corresponds to a purification of the liquid constituents. The biological or biotechnological liquid to be filtered, concentrated, purified or conditioned is, for example, a liquid that is or contains cell supernatants, blood components such as blood serum or plasma, or urine.

One aspect of the present application concerns a method for the filtration or concentration of biological macromolecules and biological microstructures. The biological materials which are present in the biotechnological liquids and are to be purified, concentrated or filtered are biological macromolecules and biological microstructures. In particular, these may be one or more of the following substances: antibodies, antibody conjugates, antibody fragment conjugates, virus particles, ribonucleic acid (RNA), deoxyribonucleic acid (DNA), plasmids, vaccines, extracellular vesicles, liposomes, secretomes, clotting factors and albumin. In the context of the present application, the extracellular vesicles are exosomes and/or microvesicles and/or apoptotic bodies. In the context of the present application, the use is for a biotechnological production method or filtration method of a biological or biotechnical liquid which is obtained from the supernatant of a cell culture or which is a supernatant of a cell culture.

According to the invention, the aim is preferably to achieve the highest possible concentration of substances to be purified, e.g. vesicles, i.e. the smallest possible quantity of liquid. It is conceivable, for example, that a batch of 9 litres is reduced according to the invention to a volume of ca. 100 ml, which leads to a corresponding increase in the density or concentration of the substances that are to be purified.

For the substrate too, i.e. for the liquid, it is possible to use liquids other than cell supernatants, e.g. blood serum or blood plasma.

The use of the invention in therapeutic methods, e.g. dialysis, is also conceivable and covered by the invention.

In a preferred embodiment of the use, according to the invention, of a filter module for a biotechnological production method, the method is a filtration method.

In a preferred embodiment of the use, according to the invention, of a filter module for a biotechnological production method, the method is a tangential flow filtration (TFF) method.

In a preferred embodiment of the use, according to the invention, of a filter module for a biotechnological production method, the method is a method for the filtration or concentration of biological macromolecules and biological microstructures, in particular extracellular vesicles, in a biotechnological liquid.

In a preferred embodiment of the use, according to the invention, of a filter module for a biotechnological production method, the method is a tangential flow filtration (TFF) method for the filtration or concentration of biological macromolecules and biological microstructures, in particular extracellular vesicles, in a biotechnological liquid.

In a preferred embodiment of the filter module according to the invention, the centrifugal pump rotor is arranged fluidically downstream or upstream on a longitudinal axis of the filter. According to one aspect, such a filter module can be used in particular for a biotechnological filtration method, in particular a tangential flow filtration (TFF) method, a method for the filtration or concentration of biological macromolecules and biological microstructures, in particular extracellular vesicles, in a biotechnological liquid, or a tangential flow filtration (TFF) method for the filtration or concentration of biological macromolecules and biological microstructures, in particular extracellular vesicles, in a biotechnological liquid.

In a preferred embodiment of the filter module according to the invention, the axis of the centrifugal pump rotor associated with the operation of the centrifugal pump rotor lies on a longitudinal axis of the filter. According to one aspect, such a filter module can be used in particular for a biotechnological filtration method, in particular a tangential flow filtration (TFF) method, a method for the filtration or concentration of biological macromolecules and biological microstructures, in particular extracellular vesicles, in a biotechnological liquid, or a tangential flow filtration (TFF) method for the filtration or concentration of biological macromolecules and biological microstructures, in particular extracellular vesicles, in a biotechnological liquid.

In a preferred embodiment of the filter module according to the invention, the filter is a dialyser for haemodialysis. This particularly advantageously makes the filter more robust to pressure differences. According to one aspect, such a filter module can be used in particular for a biotechnological filtration method, in particular a tangential flow filtration (TFF) method, a method for the filtration or concentration of biological macromolecules and biological microstructures, in particular extracellular vesicles, in a biotechnological liquid, or a tangential flow filtration (TFF) method for the filtration or concentration of biological macromolecules and biological microstructures, in particular extracellular vesicles, in a biotechnological liquid.

In a preferred embodiment of the filter module according to the invention, the centrifugal pump rotor is equipped with permanent magnets in such a way that it can be operated and/or driven in a manner supported by magnetic levitation. Supporting by magnetic levitation particularly advantageously permits the omission of mechanical bearings and therefore the omission of heat sources in proximity to a conveyed liquid. It is thus possible to avoid potential heat damage to a conveyed liquid. According to one aspect, such a filter module can be used in particular for a biotechnological filtration method, in particular a tangential flow filtration (TFF) method, a method for the filtration or concentration of biological macromolecules and biological microstructures, in particular extracellular vesicles, in a biotechnological liquid, or a tangential flow filtration (TFF) method for the filtration or concentration of biological macromolecules and biological microstructures, in particular extracellular vesicles, in a biotechnological liquid.

In a preferred embodiment of the filter module according to the invention, the housing has a first end cap, which defines an inlet flow path for a liquid L to the centrifugal pump rotor, such that a liquid L can flow into the housing perpendicular to the longitudinal axis of the filter and can be deflected such that it flows onto the centrifugal pump rotor parallel to the longitudinal axis of the centrifugal pump rotor. According to one aspect, such a filter module can be used in particular for a biotechnological filtration method, in particular a tangential flow filtration (TFF) method, a method for the filtration or concentration of biological macromolecules and biological microstructures, in particular extracellular vesicles, in a biotechnological liquid, or a tangential flow filtration (TFF) method for the filtration or concentration of biological macromolecules and biological microstructures, in particular extracellular vesicles, in a biotechnological liquid.

In a preferred embodiment of the filter module according to the invention, the housing has a first end cap, which defines an inlet flow path for a liquid L to the centrifugal pump rotor, such that a liquid L can flow into the housing perpendicular to the longitudinal axis of the filter and can be deflected such that it flows onto the centrifugal pump rotor parallel to the longitudinal axis, and the inlet flow path is designed such that the liquid flows into the centre of the centrifugal pump rotor. According to one aspect, such a filter module can be used in particular for a biotechnological filtration method, in particular a tangential flow filtration (TFF) method, a method for the filtration or concentration of biological macromolecules and biological microstructures, in particular extracellular vesicles, in a biotechnological liquid, or a tangential flow filtration (TFF) method for the filtration or concentration of biological macromolecules and biological microstructures, in particular extracellular vesicles, in a biotechnological liquid.

In a preferred embodiment of the filter module according to the invention, the housing has a first end cap, which defines an inlet flow path for a liquid L to the centrifugal pump rotor, such that a liquid can flow into the housing perpendicular to the longitudinal axis of the filter and can be deflected such that it flows onto the centrifugal pump rotor parallel to the longitudinal axis, and the centrifugal pump rotor and the end cap define a flow path such that liquid can flow centrifugally out from the centrifugal pump rotor perpendicular to the longitudinal axis of the filter and is deflected such that it thereafter flows parallel to the longitudinal axis of the filter and enters the fibres of the filter when the centrifugal pump rotor is rotated. In a development, the inlet flow path can additionally be designed such that the liquid flows into the centre of the centrifugal pump rotor. According to one aspect, such a filter module can be used in particular for a biotechnological filtration method, in particular a tangential flow filtration (TFF) method, a method for the filtration or concentration of biological macromolecules and biological microstructures, in particular extracellular vesicles, in a biotechnological liquid, or a tangential flow filtration (TFF) method for the filtration or concentration of biological macromolecules and biological microstructures, in particular extracellular vesicles, in a biotechnological liquid.

In a preferred embodiment, a filtration device according to the invention has a filter module according to the invention, which is able to be coupled to a drive unit, and a drive unit for magnetically driving the centrifugal pump rotor of the filter module, which drive unit can generate dynamic magnetic fields for magnetically driving and magnetically supporting the centrifugal pump rotor when the filter module is coupled to the drive module. During the operation of the filtration device, the filter module is coupled to the drive unit, and the drive unit generates dynamic magnetic fields which magnetically drive and/or magnetically support by levitation the centrifugal pump rotor of the filter module. According to one aspect, such a filtration device can be used in particular for a biotechnological filtration method, in particular a tangential flow filtration (TFF) method, a method for the filtration or concentration of biological macromolecules and biological microstructures, in particular extracellular vesicles, in a biotechnological liquid, or a tangential flow filtration (TFF) method for the filtration or concentration of biological macromolecules and biological microstructures, in particular extracellular vesicles, in a biotechnological liquid.

In a preferred embodiment of a use according to the invention, a filter module according to the invention or a filtration device according to the invention is used for a biotechnological filtration method for the concentration or filtration of biological macromolecules and/or biological microstructures in a biotechnological liquid. The biological macromolecules and/or biological microstructures are preferably one or more of the following substances: antibodies, antibody conjugates, antibody fragment conjugates, virus particles, ribonucleic acid (RNA), deoxyribonucleic acid (DNA), plasmids, vaccines, extracellular vesicles, liposomes, secretomes, clotting factors and albumin. The extracellular vesicles are, for example, exosomes and/or microvesicles and/or apoptotic bodies.

It will be noted at this point that the indefinite article does not necessarily refer to exactly one of the elements, although this is a possibility, but instead can also designate a plurality of the elements. Similarly, the use of the plural also includes the presence of the element in question in the singular, and, conversely, the singular also covers a plurality of the elements in question.

Further details and advantages of the invention are explained in more detail with reference to an illustrative embodiment shown in the drawing.

BRIEF DESCRIPTION OF THE DRAWINGS

The device and the method are described below with reference to the drawing, in which:

In the figures, identical or similar elements may be referred to by the same reference signs.

FIG. 1 shows a filter module 100 for the filtration of a biotechnological liquid L, having a housing 110 with a first end cap 120, a second end cap 140, and a middle part 112 between the end caps. A bundle of hollow fibres 114 is arranged therein such that it extends with its longitudinal axis from the first end cap 120 to the second end cap 140 through the middle part 112 of the housing. The first end cap 120 has a centrifugal pump rotor housing 130, in which a centrifugal pump rotor 132, preferably an impeller, is arranged. Moreover, arranged at the first end cap 120 is a first port 102, which serves to supply a biotechnological liquid to be filtered and which is fluidically connected to the interior of the hollow fibres 114 of the filter. Arranged at the second end cap 140 is a second port 104 for the removal of a biotechnological liquid L to be filtered, which port 104 is likewise fluidically connected to the interior of the hollow fibres 114 of the filter. When the device is being used for the filtration of a biotechnological liquid L, the centrifugal pump rotor 132 rotates, and it pumps the biotechnological liquid L, which flows in through the first port 102, into the cavity in the interior of the fibres 114 of the fibre bundle. Some of the liquid L passes through the fibre walls into the exterior of the fibres. The liquid that has passed through the fibres, a liquid usually regarded as waste, the permeate, can be removed through a third port 107 arranged on the filter housing 110. This third port 107 can be arranged on the first end cap 120 (as shown by 107a), on the second end cap 140 (not shown) or on the middle part 112 (shown for example by 107b). FIG. 1 shows two alternatives as to where the third port 107 can be arranged, but only one of the ports shown is required. It cannot be inferred from the depiction of two third ports 107a, 107b that this is necessary for the present application. Rather, this serves to illustrate different possibilities. The important aspect of this third port 107 is that it is fluidically connected to the exterior of the fibres of the fibre bundle 114 of the filter and that it is at the same time separated by the membrane from the interior of the hollow fibres of the fibre bundle. In the second end cap 140, the portion of the biotechnological liquid that has not passed through the fibre wall but has remained in the interior, the retentate, can leave the fibre bundle again and be removed from the filter module through the second port 104. In the course of a biotechnological filtration, a biotechnological liquid typically has to make several passes through a filter module 100 in order to achieve a desired concentration in the biotechnological liquid L. Therefore, in known biotechnological filtration arrangements, a circuit with a pump and a reservoir is often formed such that the liquid can be pumped several times through a filter module. A circuit of this kind is not shown in FIG. 1, but is shown in FIGS. 5, 6 and 7.

FIG. 2 shows a sectional view through the region of the first end cap 120 of an illustrative embodiment of a filter module 100 according to the invention. The aim here is to illustrate how the filter module 100 can be designed by way of example, in the region of the first end cap 120 and the centrifugal pump rotor housing 130, such that an inlet flow path 103 for a liquid L is formed, according to which the liquid L can flow into the housing 110 perpendicular to the longitudinal axis of the filter 114 and can be deflected such that it can however thereafter flow onto the centrifugal pump rotor 132 parallel to the longitudinal axis of the bundle of hollow fibres 114 and thus of the filter module 100. Here, reference sign 115 designates the means for fixing the fibres 114 of the fibre bundle in the housing 110. In the case of a dialyser for haemodialysis, this can involve what is called potting. Moreover, the embodiment shown in FIG. 2 is designed such that the liquid L can flow into the centre of the centrifugal pump rotor 132. Moreover, the embodiment shown in FIG. 2 is designed such that centrifugal pump rotor 132, centrifugal pump rotor housing 130 and end cap 120 define a liquid path such that liquid L can flow centrifugally out from the centrifugal pump rotor 132 perpendicular to the longitudinal axis of the filter and is deflected such that, downstream from the centrifugal pump rotor 132 and before entry into the fibres 114, it flows parallel to the longitudinal axis of the filter 114 when the centrifugal pump rotor 132 is rotated. The overall mechanical configuration of the filter housing 110 in the region of the first end cap 120, the centrifugal pump rotor 132 and the centrifugal pump rotor housing 130 results in a flow path which, in one section, can be described as being coaxial and antiparallel: In the orientation of the figure, the interior or hollow centre of the centrifugal pump rotor can be subjected to flow perpendicularly from the top downwards, pumped liquid L is conveyed radially outwards from the centrifugal pump rotor 132 when the centrifugal pump rotor 132 rotates, and it is deflected such that, in the orientation of the figure, it can thereafter flow perpendicularly upwards to the hollow fibres 114 of the fibre bundle of the filter. On the axis of the centrifugal pump rotor 132, the liquid on the inlet side of the centrifugal pump rotor 132 flows centrally downwards, coaxially and annularly about the axis of the centrifugal pump rotor 132; the liquid on the outlet side of the centrifugal pump rotor 132 flows perpendicularly upwards. A vertical arrangement of the centrifugal pump rotor and of the hollow fibres 114 of the fibre bundle affords the advantage that gas accumulations present within the liquid L are transported away upwards by buoyancy and at the same time by the liquid flow generated by the centrifugal pump rotor 132 of the pump. The above-described coaxial arrangement of centrifugal pump rotor 132 and the fibre bundle permits a particularly symmetrical flow of a liquid L through the centrifugal pump rotor 132 into the interior of the hollow fibres 114 of the fibre bundle. As will be seen from FIG. 2, antiparallel, coaxial flows of liquid exist in some sections in such a situation. The liquid flows onto the centrifugal pump rotor on the longitudinal axis of the fibre bundle, which is coincident with the rotation axis of the centrifugal pump rotor, and, after leaving the centrifugal pump rotor, is deflected such that it flows in parallel but with opposite directionality to the fibre bundle. The fibre bundle is preferably approximately cylindrical at the macroscopic level. The centrifugal pump rotor is hydraulically stabilized by this symmetrical flow arrangement. This minimizes a potential fluttering of the centrifugal pump rotor. Fluttering of the centrifugal pump rotor could lead to the biotechnological liquid being damaged. Thus, possible damage to the biotechnological liquid is also avoided. Particularly in the case of centrifugal pump rotors supported by magnetic levitation, there is also the advantage that less eccentric bearing moments occur, or the eccentric bearing moments are less strong. Therefore, less strong magnetic fields suffice for driving and supporting the centrifugal pump rotor. The less strong magnetic fields in turn mean that less energy and/or less electric current is needed in the generator of the magnetic alternating fields of the drive unit. For improved flow conduction in the substantially annular outflow region 128 of the centrifugal pump rotor 132, an optional inner supporting plate 121 can be provided in the first end cap 120. An optional seal 170 can be provided between the fibre bundle of hollow fibres 114 and the wall of the first end cap 120 or the optional potting 115.

FIG. 3 shows the same arrangement as FIG. 2, but in a perspective view. Openings 123 can additionally be seen here in an optional inner supporting plate 121 in the first end cap 120, which openings 123 are arranged between the centrifugal pump rotor 132 and the filter bundle 114 such that liquid L flows from the centrifugal pump rotor 132 through the openings 123 and then to the fibres 114 of the filter when the centrifugal pump rotor 132 has been set in rotation. Arrows indicate the flow of a biotechnological liquid L when the centrifugal pump rotor is rotating. For example, the centrifugal pump rotor 132 having a hollow centre 131 is subjected to flow such that the liquid is supplied through a central opening 134 in a disc 133 into a central cavity of the centrifugal pump rotor 132 on the rotation axis thereof.

FIG. 4 shows an illustrative embodiment of a centrifugal pump rotor according to the invention. This takes the form of an impeller rotor with a hollow centre. The figure illustrates how the blades 135 of the centrifugal pump rotor can for example be bent, for example in a spiral shape. The blades are arranged between two discs, wherein the lower disc in the figure adjoins the permanent magnets 136 arranged in the centrifugal pump rotor, and the upper disc 133 has a central opening 134 through which liquid to be pumped can flow into the hollow centre of the centrifugal pump rotor 132.

FIG. 5 shows schematically the flow diagram of an embodiment of a filtration device 1100 according to the invention. Besides the filter module 100, there are, for example, a runoff 300 and a reservoir 200 for the liquid L. The filtration arrangement 1100 is set up as a circuit for the biotechnological liquid L that is to be filtered or purified. This figure shows a biotechnological filtration arrangement 1100 formed as a circuit having a pump with a centrifugal pump rotor 132 and having a reservoir for the biotechnological liquid L circulating in the circuit, wherein a liquid L to be filtered can be pumped several times through a filter module 100. The dotted line indicates that the centrifugal pump rotor and the filter with the bundle of hollow fibres 114 are arranged in a common filter housing 110. The figure does not show the drive unit to which the filter module 100 is able to be coupled and which can generate dynamic magnetic fields that can magnetically drive and/or magnetically support by levitation the centrifugal pump rotor 132, since the latter has permanent magnets.

FIG. 6 shows schematically the flow diagram of a particular embodiment of a filtration device 1200 according to the invention. Here, the filter of the filter module 100 is constructed like a known dialyser for haemodialysis. Compared to filters of the kind commonly used in biotechnological filtration devices, a dialyser particularly advantageously has a fibre arrangement that is more stable with respect to pressure differences: The fibres 114 have, in relation to the external diameter, a smaller fibre internal diameter. This provides the increased stability of the hollow-fibre membranes. In addition, the fibres 114 of a dialyser are typically shorter, which also results in increased stability. In order to compensate for the shorter fibres 114 and the thicker membrane walls, as regards the filtration yield, a dialyser has a larger number of fibres 114. Through the use of a dialyser as a filter in the filter module 100, and from the increased stability with respect to pressure differences inside/outside the fibres 114, an additional pump 400 can be arranged such that it is connected to the port 107 for the removal of precipitated waste liquid, which is fluidically connected to the exterior of the hollow fibres 114. The pumping direction is chosen such that the permeate is sucked from the exterior of the fibres 114. If the additional pump 400 were operated in known filtration devices, such an arrangement would lead to the membranes being damaged. Particularly advantageously, the arrangement of this additional pump 400 at the port 107 for permeate removal has the effect of allowing a defined concentration to be achieved with fewer passes of the biotechnological liquid L to be concentrated than would be the case without the additional pump 400. On the one hand, the time needed to reach a defined concentration is thus particularly advantageously reduced. On the other hand, a particular advantage is that the biotechnological liquid L is subjected to fewer passes through the filter, and thus experiences less damage. The more often a biotechnological liquid passes through a filter, the greater the potential damage. A further advantage of this arrangement is that the additional pump 400 does not cause any additional damage to the biotechnological liquid L that is to be concentrated: The additional pump 400 comes into contact only with the permeate, which is a waste product.

FIG. 7 shows the flow diagram of a filtration device 1300 from FIG. 6, additionally with an optional check valve 500, which is arranged downstream from the additional pump 400, at the port 107 for removal of permeate. The check valve 500 is located on the permeate line between the additional pump 400 and the runoff 300.

Figure 1:
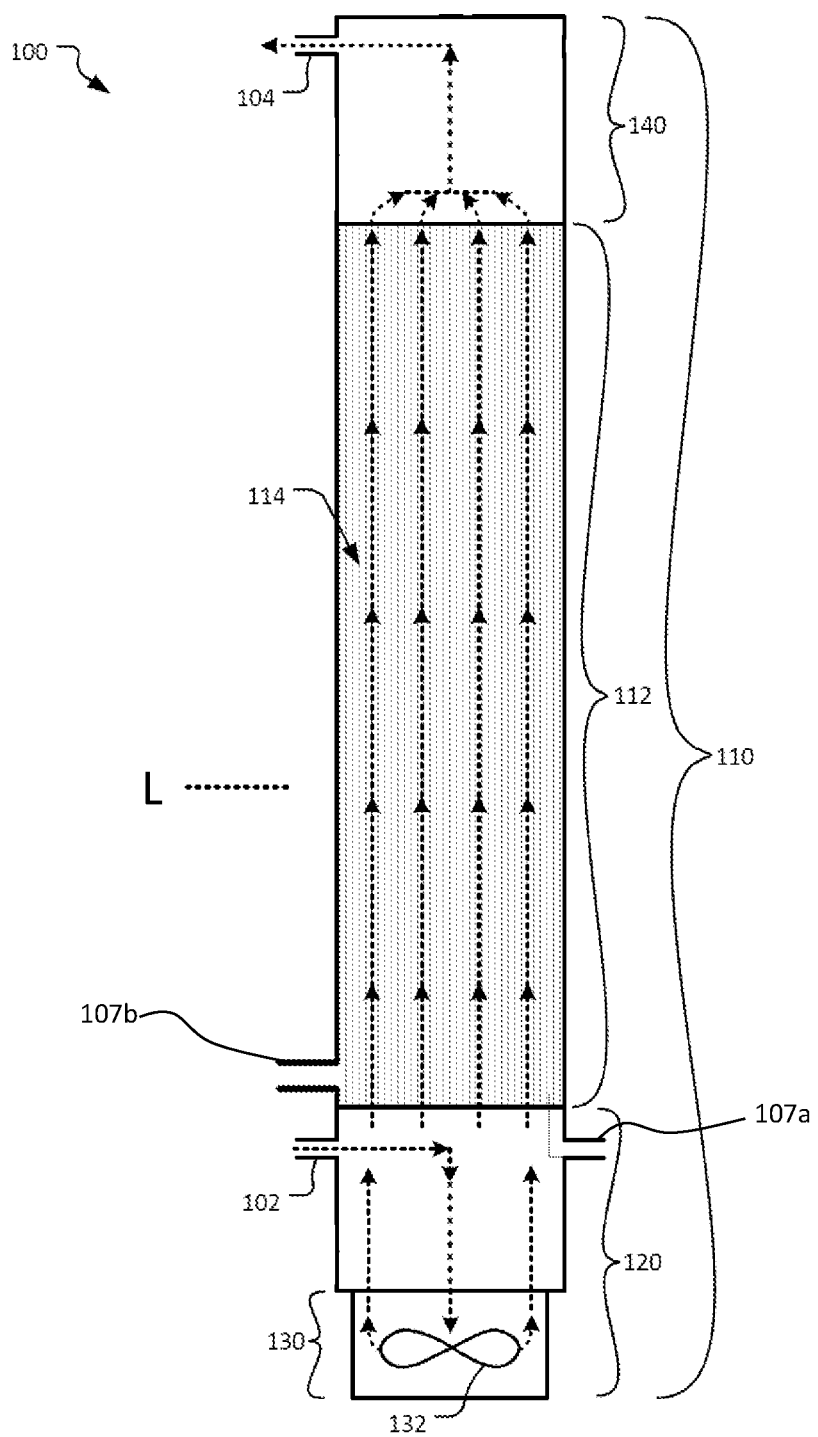
FIG. 1 shows a schematic representation of a filter module according to the invention for use for filtration of a biotechnological liquid (in a first embodiment)
Figure 2:
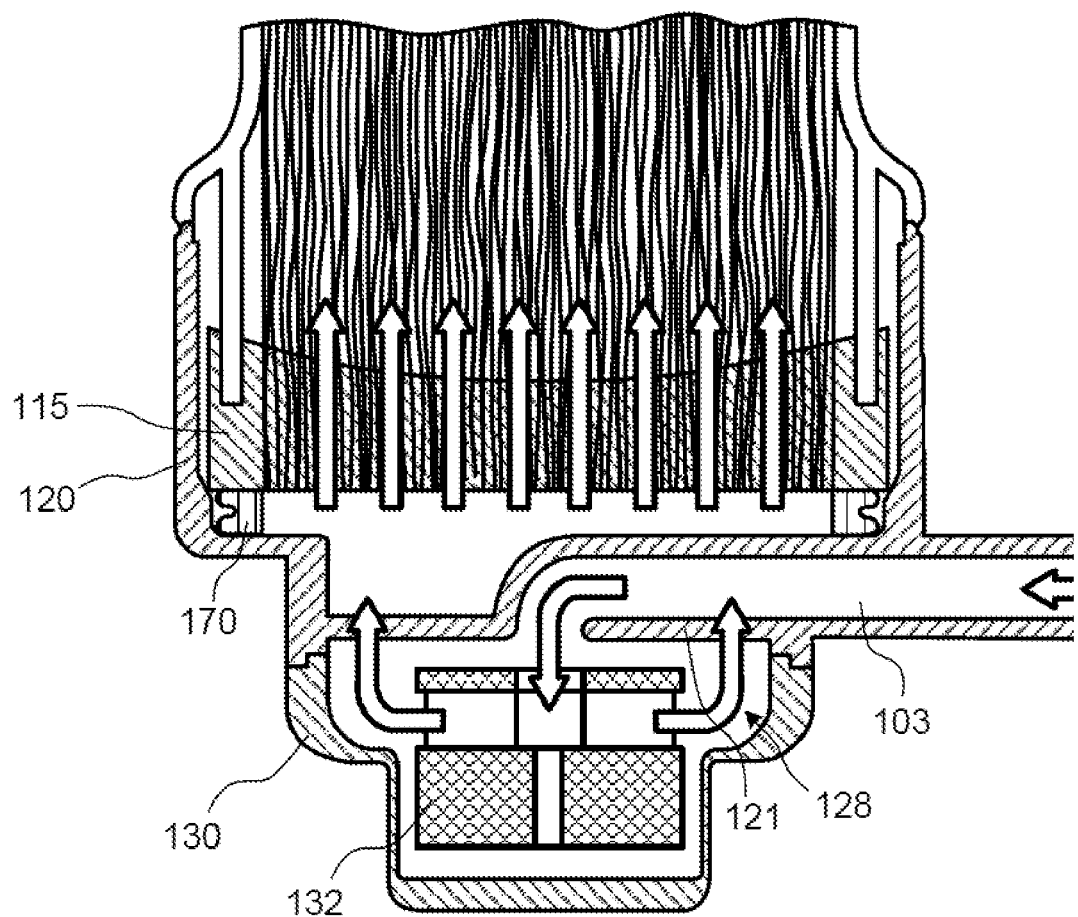
FIG. 2 shows a sectional view through the region of the first end cap of an illustrative embodiment of a filter module according to the invention.
Figure 3:
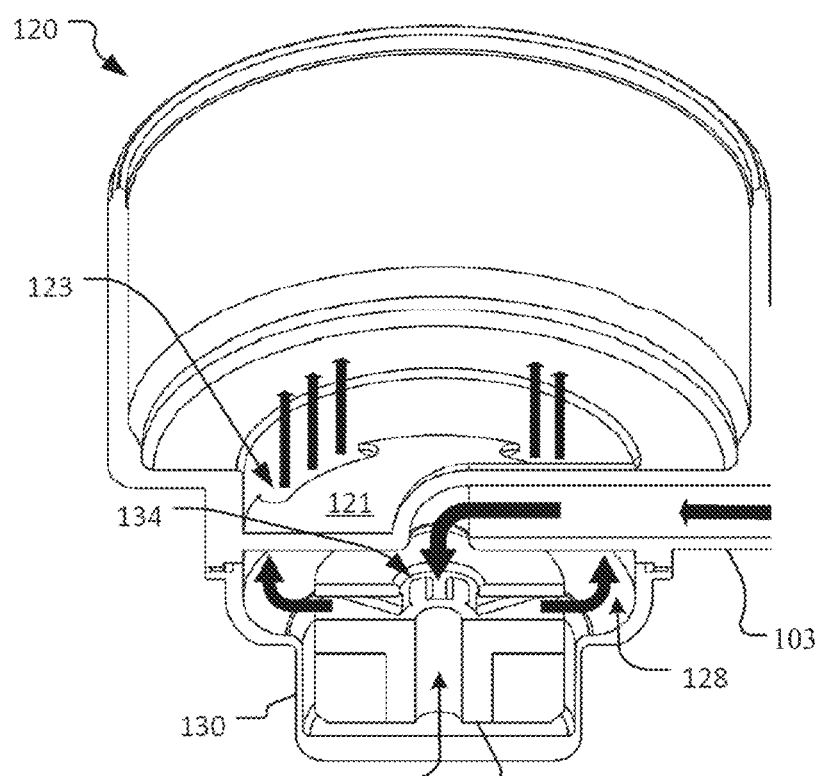
FIG. 3 shows the same arrangement as in FIG. 2, but in a perspective view, wherein an optional inner supporting plate with openings can additionally be seen in the first end cap.
Figure 4:
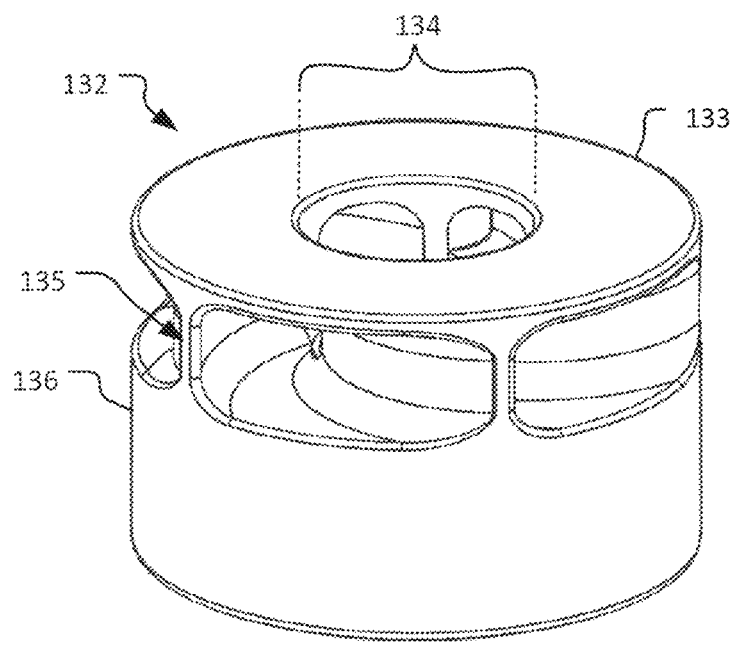
FIG. 4 shows an illustrative embodiment of a centrifugal pump rotor according to the invention.
Figure 5:
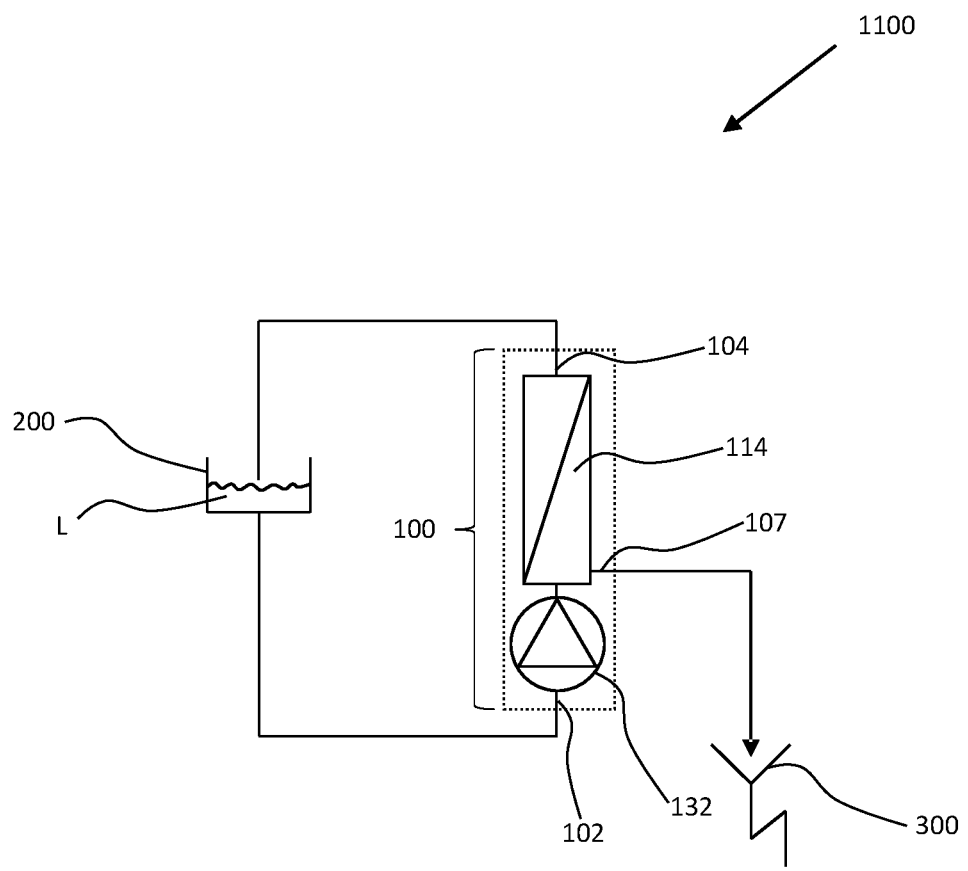
FIG. 5 shows the flow diagram of an illustrative embodiment of a filtration device according to the invention, as employed in a use, according to the invention, of a filter module having, in a filter housing, a filter, with a bundle of hollow fibres, and a centrifugal pump rotor, for a biotechnological production method.
Figure 6:
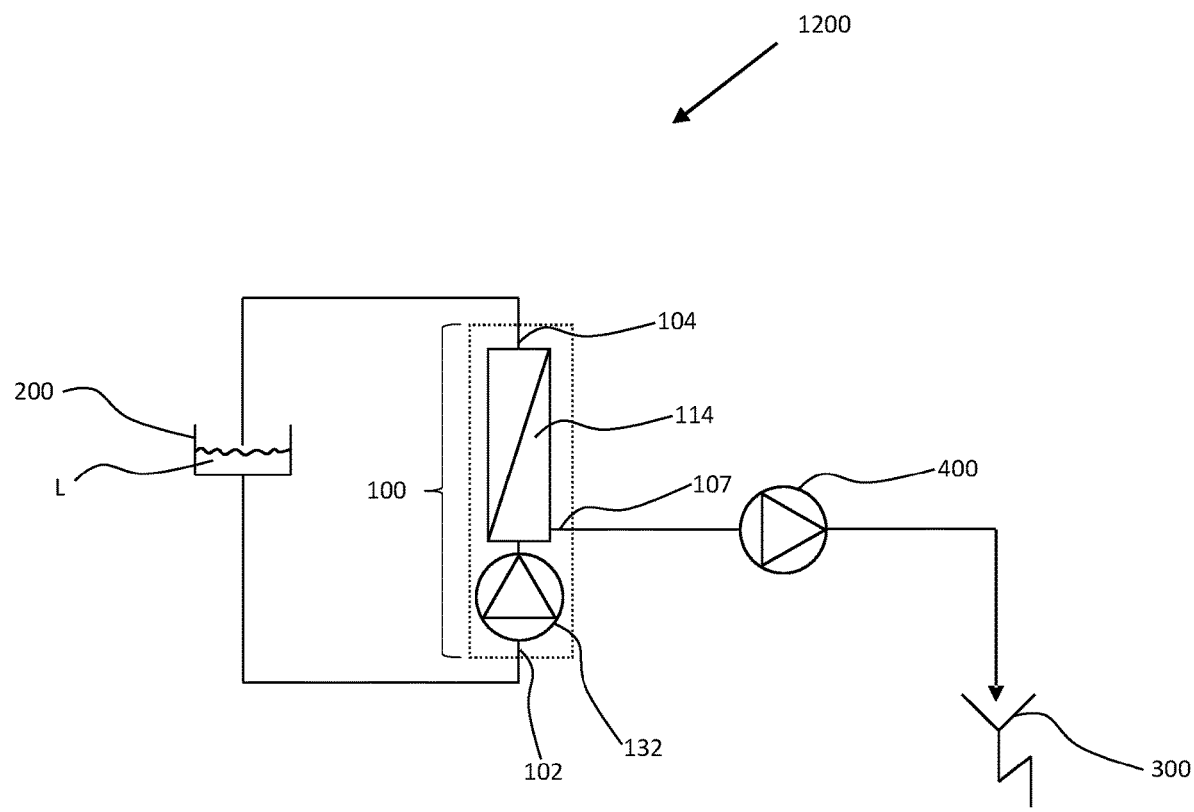
FIG. 6 shows the flow diagram of a particular embodiment of a filtration device according to the invention in which the filter of the filter module is constructed like a known dialyser for haemodialysis, wherein the filtration device has an additional pump downstream from the permeate port.
Figure 7:
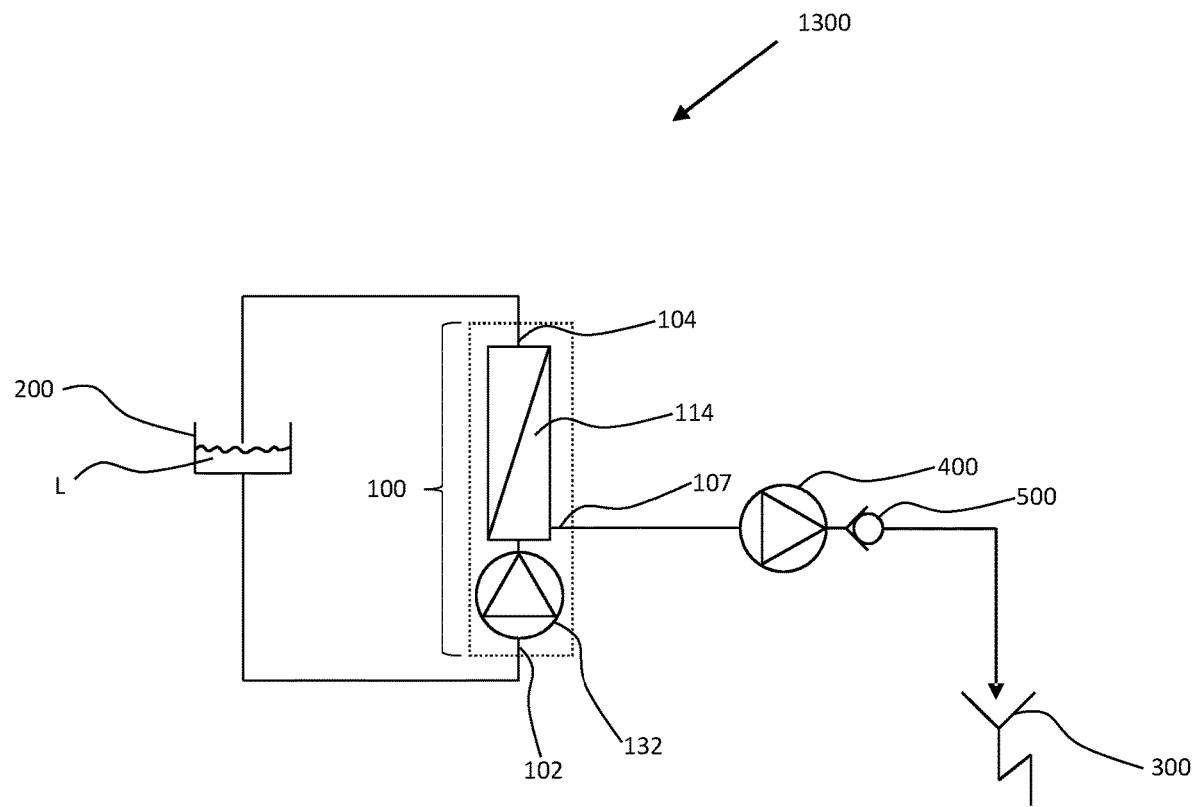
FIG. 7 shows the flow diagram from FIG. 6, additionally with an optional check valve, which is arranged downstream from the additional pump at the port for removal of permeate.

By virtue of this optional, additional check valve 500, the pressure ratios at the membrane of the filter can be adjusted, particularly advantageously in interaction with the additional pump 400. To this end, a check valve 500 is used which opens when subjected to a suitably chosen minimum pressure from the additional pump 400.

The invention claimed is:

1. A method for processing of biotechnological liquids, said method comprising passing a biotechnological liquid through a filter module, said filter module comprising a filter housing, and a filter, with a bundle of hollow fibres, and a centrifugal pump rotor in said filter housing, wherein an inlet flow path is defined such that the biotechnological liquid is flowable into the filter housing to the centrifugal pump rotor, the inlet flow path being perpendicular to a longitudinal axis of the filter, the inlet flow path is designed such that the biotechnological liquid flows into a hollow centre of the centrifugal pump rotor and the biotechnological liquid is deflected such that the biotechnological liquid thereafter flows parallel to the longitudinal axis of the filter and enters the hollow fibers of the filter by the centrifugal pump rotor forcing the biotechnological liquid into the hollow fibres, wherein the biotechnological liquid flows through the hollow fibres parallel to the longitudinal axis of the filter.

2. The method of claim 1, wherein the method is a filtration method.

3. The method of claim 2, wherein the method is a tangential flow filtration (TFF) method.

4. The method of claim 3, wherein the method is a method for the filtration or concentration of biological macromolecules and biological microstructures.

5. The method of claim 1, wherein the method is a tangential flow filtration (TFF) method for the filtration or concentration of biological macromolecules and biological microstructures.

6. The method of claim 3, wherein the method is a method for the filtration or concentration of extracellular vesicles in the biotechnological liquid.

7. The method of claim 4, wherein the method for the filtration or concentration of extracellular vesicles in the biotechnological liquid.

8. The method of claim 1, wherein the filter housing has a first end cap that defines the inlet flow path, wherein the biotechnological liquid is deflectable such that the biotechnological liquid flows onto the centrifugal pump rotor parallel to the longitudinal axis.

9. The method of claim 1, wherein the filter module further comprises a first port for the supply of the biotechnological liquid to be filtered, which said first port is fluidically connected to the interior of the hollow fibres and a first end cap that defines the inlet flow path for the biotechnological liquid.

10. A filter module for filtration of a biotechnological liquid, said filter module comprising:
   a. a filter housing,
   b. a filter arranged in the filter housing with a bundle of hollow fibres,
   c. a centrifugal pump rotor arranged in the filter housing such that the centrifugal pump rotor is fluidically connected to an interior of the hollow fibres, wherein the centrifugal pump rotor is able to be magnetically driven and the centrifugal pump rotor is configured to force the biotechnological liquid into the hollow fibres such that the biotechnological liquid flows through the hollow fibres parallel to a longitudinal axis of the filter,
   d. a first port for the supply of the biotechnological liquid to be filtered, which said first port is fluidically connected to the interior of the hollow fibres, wherein an inlet flow path is defined such that the biotechnological liquid is flowable into the filter housing to the centrifugal pump rotor, the inlet flow path being perpendicular to the longitudinal axis of the filter, and the inlet flow path is designed such that the biotechnological liquid flows into a hollow centre of the centrifugal pump rotor and the biotechnological liquid is deflected such that the biotechnological liquid thereafter flows parallel to the longitudinal axis of the filter and enters the hollow fibres of the filter by the centrifugal pump rotor forcing the biotechnological liquid into the hollow fibres,
   e. a second port for the removal of the biotechnological liquid to be filtered, which said second port is fluidically connected to the interior of the hollow fibres,
   f. a third port for the removal of precipitated waste liquid, which said third port is fluidically connected to an exterior of the hollow fibres.

11. The filter module according to claim 10, wherein the centrifugal pump rotor is arranged fluidically downstream or upstream on the longitudinal axis of the filter.

12. The filter module according to claim 11, wherein a longitudinal axis of the centrifugal pump rotor associated with the operation of the centrifugal pump rotor lies on the longitudinal axis of the filter.

13. The filter module according to claim 10, wherein the filter is a dialyser for haemodialysis.

14. The filter module according to claim 10, wherein the centrifugal pump rotor is equipped with permanent magnets in such a way that the centrifugal pump rotor is operable and/or driven in a manner supported by magnetic levitation.

15. The filter module according to claim 10, wherein the filter housing has a first end cap that defines the inlet flow path, wherein the biotechnological liquid is deflectable such that the biotechnological liquid flows onto the centrifugal pump rotor parallel to the longitudinal axis.

16. The filter module according to claim 15, wherein the centrifugal pump rotor and said first end cap define a liquid path such that the biotechnological liquid is flowable centrifugally out of the centrifugal pump rotor perpendicular to the longitudinal axis of the filter.

17. A filtration device comprising
   a. the filter module according to claim 10, which is able to be coupled to a drive unit, and
   b. said drive unit for magnetically driving the centrifugal pump rotor of the filter module, which drive unit is capable of generating dynamic magnetic fields for magnetically driving and magnetically supporting the centrifugal pump rotor when the filter module is coupled to the drive unit.

18. A method for filtration or concentration of biotechnological liquids, said method comprising passing a biotechnological liquid through said filtration device of claim 17 to achieve concentration or filtration of biological macromolecules and/or biological microstructures in said biotechnological liquid.

19. A method for filtration or concentration of biotechnological liquids, said method comprising passing a biotechnological liquid through said filter module according to claim 6 to achieve concentration or filtration of biological macromolecules and/or biological microstructures in said biotechnological liquid.

* * * * *